United States Patent
Zanella et al.

(10) Patent No.: US 9,224,198 B2
(45) Date of Patent: Dec. 29, 2015

(54) ANALYSIS OF THE DIGITAL IMAGE OF THE SURFACE OF A TYRE AND PROCESSING OF NON-MEASUREMENT POINTS

(75) Inventors: Jean-Paul Zanella, Clermont-Ferrand (FR); Claire Moreau, Clermont-Ferrand (FR); Guillaume Noyel, Clermont-Ferrand (FR); Yusi Shen, Clermont-Ferrand (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 0 days.

(21) Appl. No.: 14/112,452

(22) PCT Filed: Mar. 21, 2012

(86) PCT No.: PCT/EP2012/055015
§ 371 (c)(1),
(2), (4) Date: Mar. 12, 2014

(87) PCT Pub. No.: WO2012/143197
PCT Pub. Date: Oct. 26, 2012

(65) Prior Publication Data
US 2014/0185883 A1    Jul. 3, 2014

(30) Foreign Application Priority Data
Apr. 18, 2011  (FR) .................. 11 53343

(51) Int. Cl.
*G06K 9/00*   (2006.01)
*G06T 7/00*   (2006.01)
(Continued)

(52) U.S. Cl.
CPC .............. *G06T 7/0008* (2013.01); *G06T 5/005* (2013.01); *G06T 7/408* (2013.01);
(Continued)

(58) Field of Classification Search
CPC ................ G06T 7/0008; G06T 7/408; G06T 2207/30164
See application file for complete search history.

(56) References Cited

U.S. PATENT DOCUMENTS

| 4,951,676 A | 8/1990 | Collet-Billon ........... 128/660.01 |
| 2001/0013823 A1 | 8/2001 | Hatakeyama et al. ......... 340/3.1 |

(Continued)

FOREIGN PATENT DOCUMENTS

WO    WO 03/023699 A1    3/2003

OTHER PUBLICATIONS

R. A. Peters, "A New Algorithm for Image Noise Reduction Using Mathematical Morphology," IEEE Transactions on Image Processing, vol. 4, No. 5, pp. 554-568 (1995).

(Continued)

*Primary Examiner* — Samir Ahmed
(74) *Attorney, Agent, or Firm* — Fitzpatrick, Cella, Harper & Scinto

(57) ABSTRACT

In a method for processing an image of a surface of a tire, a 3D digital image of the surface is captured, and each pixel of the captured image is assigned a grey level value proportional to an elevation of a corresponding point with respect to the surface. The pixels are placed in rows and columns. A search is made for zones of the surface that include pixels having a grey-level value lower than a given threshold. Boundaries of an encompassing box that includes one or more of the zones are determined. Inside the encompassing box, a grey-level value equal to a mean grey-level value of a set of reference pixels ($K_{ij}$, $s_i$) positioned in a zone situated in immediate proximity to a pixel under consideration is assigned to each of the pixels whose grey-level value is lower than the given threshold.

8 Claims, 4 Drawing Sheets

(51) Int. Cl.
*G06T 5/00* (2006.01)
*G06T 7/40* (2006.01)
*G01N 21/89* (2006.01)
*G01N 21/95* (2006.01)

(52) U.S. Cl.
CPC ........... *G01N 21/8914* (2013.01); *G01N 21/95* (2013.01); *G06T 2207/10028* (2013.01); *G06T 2207/30164* (2013.01)

(56) References Cited

U.S. PATENT DOCUMENTS

| | | | | |
|---|---|---|---|---|
| 2003/0012453 | A1 | 1/2003 | Kotlikov et al. | 382/275 |
| 2004/0071334 | A1* | 4/2004 | Hassler et al. | 382/141 |
| 2005/0259859 | A1* | 11/2005 | Hassler et al. | 382/141 |
| 2007/0209431 | A1* | 9/2007 | Fujisawa et al. | 73/146 |
| 2008/0218742 | A1* | 9/2008 | Sakoda et al. | 356/73 |
| 2008/0319706 | A1 | 12/2008 | Uffenkamp et al. | 702/150 |
| 2011/0013823 | A1* | 1/2011 | Joly | 382/141 |
| 2011/0018999 | A1* | 1/2011 | Joly et al. | 348/148 |
| 2011/0019903 | A1* | 1/2011 | Joly et al. | 382/141 |
| 2011/0069323 | A1* | 3/2011 | Takahashi et al. | 356/625 |
| 2013/0202156 | A1 | 8/2013 | Joly et al. | 283/104 |
| 2013/0208949 | A1 | 8/2013 | Joly et al. | 382/103 |

OTHER PUBLICATIONS

P. Salembier et al., "Hierarchical Morphological Segmentation for Image Sequence Coding," IEEE Transactions on Image Processing, vol. 3, No. 5, pp. 639-651 (1994).

J. Oh et al., "Ranked Directional Morphological Filtering of Impulse Noise in Images," Proceedings of the IEEE International Conference on Acoustics, Speech, and Signal Processing, vol. 6, pp. 2167-2170 (2000).

Z. Tauber et al., "Review and Preview Disocclusion by Inpainting for Image-Based Rendering," IEEE Transactions on Systems, Man, and Cybernetics: Part C: Applications and Reviews, vol. 37, No. 4, pp. 527-540 (2007).

J. Davis et al., "Filling Holes in Complex Surfaces using Volumetric Diffusion," Proceedings of the First International Symposium on 3D Data Processing Visualization and Transmission, 15 pages (2002).

Li Jie, "Detecting Tire Tread Morphology Based on Laser Triangulation," Master's Thesis (full document), Changchun University of Science and Technology (Feb. 15, 2010).

Dong Jiyang et al., "A Simple Algorithm for Removing Salt and Pepper Noise from Gray-scale Image," Computer Engineering and Applications, vol. 20, pp. 27-29 (2003).

* cited by examiner

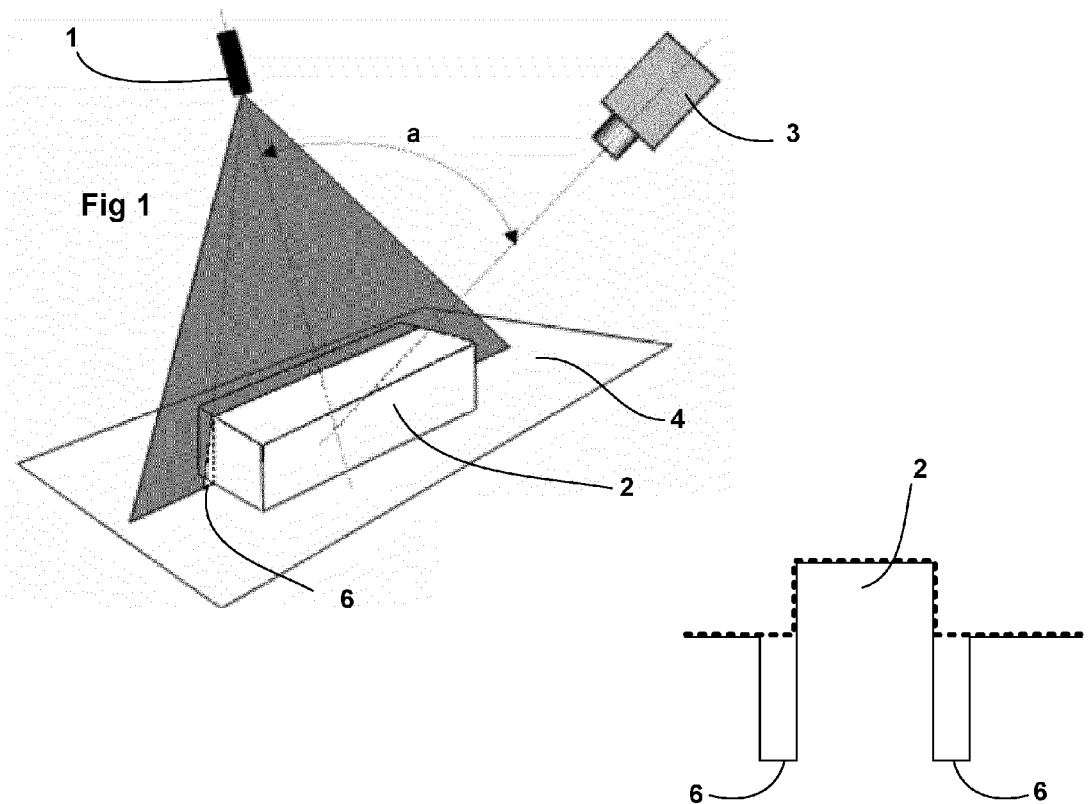
Fig 1
Fig 3
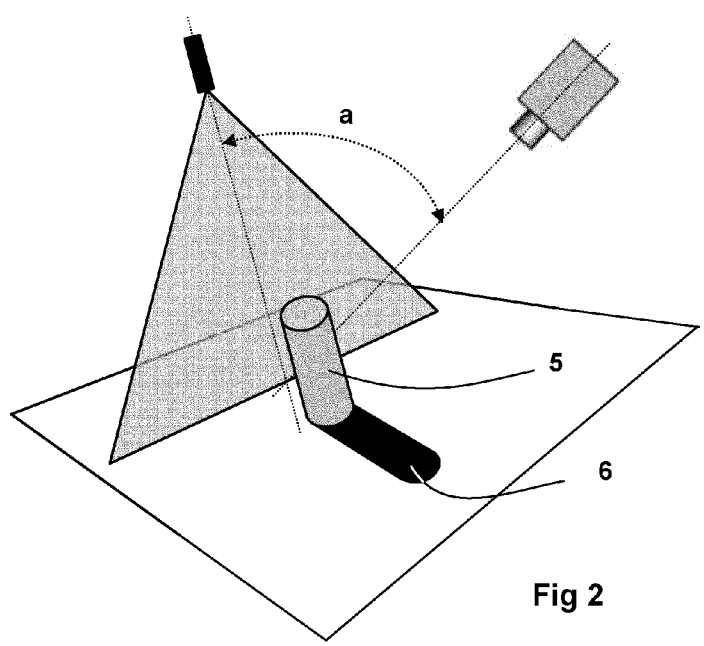
Fig 2

ANALYSIS OF THE DIGITAL IMAGE OF THE SURFACE OF A TYRE AND PROCESSING OF NON-MEASUREMENT POINTS

FIELD OF THE INVENTION

The invention relates to the field of the manufacture of tyres, and more particularly the field of the automatic inspection of the surface of a tyre with a view to establishing a diagnosis of compliance with respect to pre-established references.

RELATED ART

One of the steps of this process consists, in a known manner, in acquiring the three-dimensional image of the surface of the tyre.

The acquisition of this image is carried out with the aid of means based on the principle of optical triangulation, using for example a 2D sensor coupled with a light source of the laser type.

The topographical image of the tyre surface is in fact a two-dimensional image, called a grey-level image, in which, with every point, i.e. with every pixel (x, y) of the image, is associated a value f(x, y), called grey level, and usually between 0 and 255. This grey level value may usefully be encoded on 8 or 16 bits for a better dynamic. The grey level represents the altitude of this point relative to the surface. For encoding on 8 bits, the value 255 (white) corresponds to the highest altitude, and the value 0 (black) corresponds to the lowest altitude. As a general rule, the pixels of the image are placed in rows and in columns.

It is however observed that the image of the surface arising from these acquisition means can exhibit non-measurement points that it is necessary to tag and to remove before undertaking the subsequent digital processings. Otherwise, the analysis algorithms could incorrectly consider these zones to be structural anomalies of the tyre to be inspected.

These points have the characteristic of exhibiting a zero or very low value. They appear mainly in the zones of strong relief in which the camera cannot see the laser streak because of the shadow zones engendered by the profile, or else in proximity to the vents present on the sidewalls or on the sculptures because of the shadow cast by these protuberances on the immediately surrounding surface of the tyre.

BRIEF DESCRIPTION OF EMBODIMENTS OF THE INVENTION

The object of the method for processing the three-dimensional digital image of the surface of a tyre is to detect and to eliminate these non-measurement points with the aim of not disturbing the subsequent digital processings intended for example to identify the anomalies present on the surface of the tyre.

According to the invention, the method for processing the image envisages the steps in the course of which:
 a search is made for the zones of the surface to be inspected comprising pixels whose grey level value is lower than a given threshold,
 the boundaries of an encompassing box comprising one or more zones of pixels whose grey level value is lower than a given threshold are determined,
 inside the encompassing box, a grey level value equal to the mean grey level value of a set of reference pixels placed in a zone situated in immediate proximity to the pixel considered is assigned to each of the pixels whose grey level value is lower than a given threshold.

The method can envisage that the set constituting the reference pixels is formed by a reference matrix comprising an odd number of rows and of columns. Preferably, the reference matrix comprises fewer than ten rows and fewer than ten columns. In this configuration, each point of the encompassing box is modified by assigning to a given point the mean grey level value of the pixels of the reference matrix centred on the said point. Preferably the points of the encompassing box are processed successively in ascending order of the rows and columns.

This applies in particular in the case of the zones of small area that it is possible to reduce simply by applying this particular type of moving recursive average.

When the zone containing the non-measurement points is more extensive, there will then be chosen a set of reference pixels for a given row included in the reference box and secant to the zone containing pixels having a grey level value lower than the given threshold, which is formed by the pixels of a reference segment belonging to the said row. Preferably, the reference segment does not contain any pixels having a grey level value lower than the given threshold, and its length lies between 5 and 30 pixels. In this configuration, the mean grey level value of the pixels of the reference segment is assigned to the set of pixels of the row containing the said reference segment and having a grey level value lower than the given threshold.

It is however observed that these zones of non-measurement points whose area is greater than a certain threshold are as a general rule formed by the cast shadow of a vent. Knowing the shape and the general configuration of the vents, it is then possible to refine the method by envisaging steps in the course of which:
 the area of the zone of pixels having a grey level value lower than the given threshold is determined,
 when the area of this zone exceeds a given threshold, the angle between the principal axis of the said zone and the direction of the rows of pixels is determined,
 the centre of gravity of the said surface is determined,
 a search is made for the position of a vent at one of the ends of the principal axis of the said zone, and the zone is oriented in a direction OX extending over the principal axis of the zone and having the foot of the vent as origin,
 to each of the rows secant to the zone containing the pixels having a grey level value lower than the given threshold, is assigned a reference segment placed on the side of the principal axis of the said zone corresponding to the angular sector making a positive angle g with the direction of the shadow zone.

When the angle between the principal axis of the said surface and the direction of the rows of pixels is less than 5°, the mean grey level value of the pixels of the reference segment is assigned to the set of pixels of the row containing the said reference segment and lying between the middle of the reference segment and the intersection of the said row of pixels with the contour of the vent.

When the angle between the principal axis of the said surface and the direction of the rows of pixels is greater than 5°, and only for the rows lying between the centre of gravity and the vent, the mean grey level value of the pixels of the reference segment is assigned to the set of pixels of the row containing the said reference segment, and lying between the middle of the reference segment and the intersection of the row with the contour of the vent.

Finally, when the angle between the principal axis of the said surface and the direction of the rows of pixels is greater than 5°, and for the rows which do not lie between the centre of gravity and the vent, the mean grey level value of the pixels of the reference segment is assigned to the set of pixels of the row containing the said reference segment and lying between the middle of the reference segment and the pixel of the said row whose grey level value is lower than the mean grey level value of the pixels of the reference segment.

BRIEF DESCRIPTION OF THE DRAWINGS

The object of the description which follows is to describe in detail the various steps of the method according to the invention, supported by FIGS. 1 to 5 in which:

FIGS. 1 and 2 represent a schematic view of a means for capturing the image of the surface of a tyre, FIG. 3 illustrates in a schematic manner the causes giving rise to the appearance of the non-measurement points.

DETAILED DESCRIPTION OF EMBODIMENTS OF THE INVENTION

Figure 4:
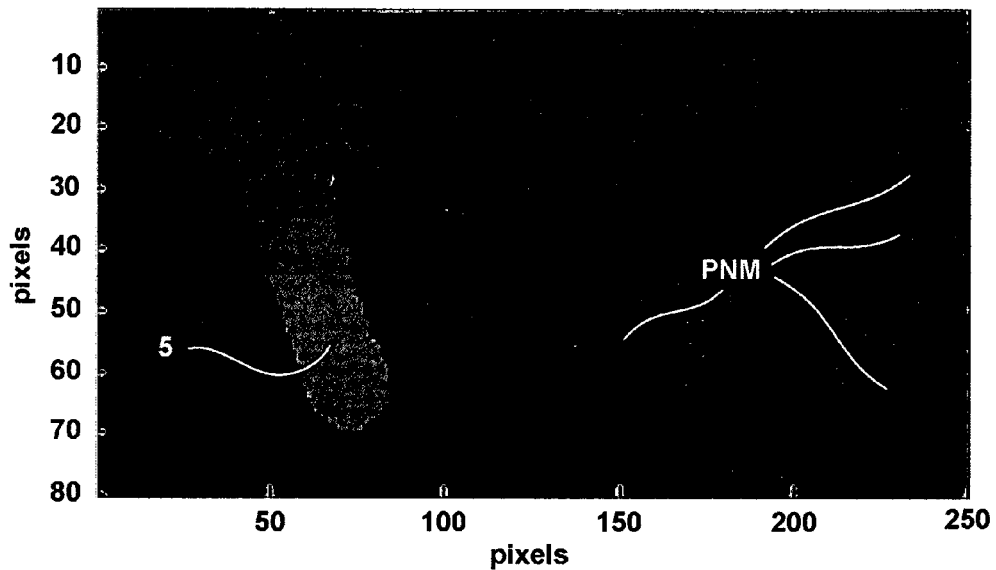
FIG. 4 represents the partial image of the surface of a tyre exhibiting non-measurement points.

The acquisition of the image of the surface of a tyre is illustrated by FIGS. 1 and 2. This acquisition is effected, by way of example, with the aid of a slit light emitted by a laser 1 and of a camera 3 able to capture the 2D image of the illuminated surface. The camera is positioned such that its direction of aim forms a given angle a with the beam emitted by the laser source. By triangulation, it is then possible to determine the coordinates of the relief element 2 relative to the supporting surface 4. As a general rule, the slit light is directed in an axial or radial direction perpendicularly to the circumferential direction corresponding to the direction of the rotation imposed on the tyre to input a complete image of its surface.

FIG. 1 represents a configuration in which the device captures the image of a relief element 2, and FIG. 2 the configuration in which the relief element is a vent. The non-measurement points 6 appear in the shadow zones not illuminated by the laser beam. In the absence of returning light, these points are considered to have a zero or very low altitude and appear black on the image representing the surface. FIG. 3 illustrates the representation, in cross-section, of the relief of FIG. 1 in which the measured relief appears as a continuous line, whereas the actual profile appears dashed. Hence, location of the non-measurement points can be achieved simply by searching in the image for the pixels whose grey level value, representing the altitude of the corresponding point with respect to the surface to be inspected, is lower than a given threshold or indeed zero.

FIG. 4 is a grey level image of the surface of a tyre on which appear by contrast zones comprising non-measurement points, easily identifiable in that their grey level is zero or much lower than a predetermined threshold value. In this specific case, these points originate from the shadow cast by a vent 5 (at the centre of the image) or points lying alongside a relief (on the right of the image). It is observed that the shape and the area of these zones are of different nature, respectively significant and elongated for the shadow of the vent, and small and of granular form for the edge of a relief.

The processing of this image to remove these non-measurement points conforms, broadly, to the same basic principles, but will seek to exploit the peculiarities of these two particular morphologies so as to optimize the quality of the processings.

Figure 5:
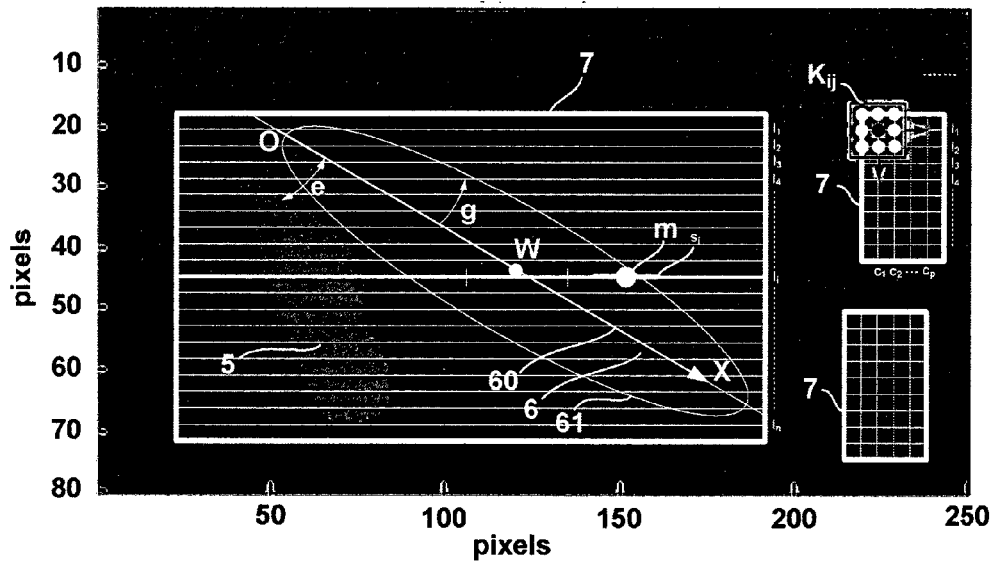
FIG. 5 illustrates the image processings used by the method according to the invention.

The first step of the processing, after having identified the non-measurement points, consists in framing the zones containing these points with an encompassing box. For the sake of simplicity in the execution of the computations the said box can advantageously be of rectangular shape, and be aligned with the rows and the columns of pixels forming the image to be processed. FIG. 5 makes it possible to view the zones containing non-measurement points surrounded by an encompassing box 6, comprising n rows ($l_1, l_2, l_3, l_4 \ldots$) and p columns ($c_1, c_2, \ldots c_p$).

The subsequent processing consists in assigning to each of the non-measurement points a grey level value equal to the average of the grey level value of the pixels situated in immediate proximity to the pixel considered. It is indeed admitted that the non-measurement points are situated substantially at the same altitude as their direct neighbours with which they are aligned.

A first mode of processing consists in assigning to a pixel the mean value of the pixels situated directly around it. This mode of processing is particularly advantageous for correcting the non-measurement points included in zones of small area as is illustrated in the right part of the image of FIG. 5.

For this purpose, a set of reference pixels is determined, formed by a reference matrix $K_{ij}$ comprising an odd number of rows and of columns, and whose central value is positioned on the pixel to be modified.

Typically, having regard to the relatively small area of these zones, a matrix of size 3×3 or 7×7 will be chosen.

The processing then consists in calculating the average of the grey level values of the points of the matrix, including the central value, and of replacing the grey level value of the central value by the newly computed mean value.

This operation is done preferably in a sliding manner, beginning with the pixel situated, for example, at the top left of the encompassing box, and by processing column by column in the manner indicated hereinabove all the points of the upper row. We then drop down one row and repeat the same operation on all the pixels of this row until the pixel of the last row and of the last column included in the encompassing box.

It will be observed that the computed averages successively replace the pixels whose grey level value is lower than the predetermined threshold and that these computed averages enter in their turn into the determination of the grey level value of the following pixels, hence the recursive character of this moving average over the whole of the encompassing box.

So as to obtain a stable result, the limits of the encompassing box will preferably be placed so that the pixels representing the non-measurement points closest to these boundaries are placed a few pixels away.

The second mode of processing deals more particularly with the resulting non-measurement points of the shadow cast by a vent on the surface of the tyre.

It is observed in the image of FIG. 5 that the shape of this shadow 6 is as a general rule highly elongated and occupies a relatively significant area facing the surface of the previously described zones. This assumption is satisfied by ensuring that the area of the shadow zone is greater than a predetermined threshold, and the centre of gravity W of the surface formed by the non-measurement points is located.

The operations which follow are therefore specific to this type of anomaly, considering moreover that, in the case of a tyre, these zones cannot coincide with other types of zones containing non-measurement points.

After having determined the contours of the encompassing box 7, of rectangular shape and preferably positioned according to the ordering of the rows and columns of pixels, a search is made for the angle formed by the principal axis of the zone of non-measurement points with the direction of the rows. Accordingly, an ellipse 61 containing the said shadow zone is fitted, and the major axis 60 of the ellipse is likened to the direction of the axis of inertia of the said shadow zone, which makes an angle g with the direction of the rows.

A search is then made for the foot of the vent 5 at one of the two ends of the principal axis of the zone containing the non-measurement points. This makes it possible to give the principal axis an orientation in a direction OX extending along the zone and having the foot of the vent as origin, as is represented in FIG. 5.

The following step consists in determining the reference pixels which will be used to compute the mean grey level value to be assigned to the non-measurement points.

In contradistinction to the first mode of processing, the reference pixels consist, in this second case, of reference segments $s_i$ each contained in a row $l_i$ and comprising around some twenty or so pixels.

The said reference segment should then be positioned in a judicious manner for each of the rows $l_i$. Indeed, preferably, matters are arranged so that this segment $l_i$ is placed on the side of the principal axis 60 corresponding to the angular sector making a positive angle g with the direction OX of the shadow zone 6. Stated otherwise, the reference segments should preferably be positioned on the opposite side from the general direction of the projection of the vent on the surface, so as to permit, as will be seen subsequently, complete processing of all the points of the zone containing the non-measurement points.

Matters are also arranged so that the segment is positioned in proximity to the edge of the zone of non-measurement points, and so that it does not contain any non-measurement points.

The average of the grey level values of the pixels contained in the reference segment is thereafter computed. This mean grey level value is then allocated to the pixels of the zone containing the non-measurement points of the row $l_i$ corresponding to the reference segment $s_i$.

Figure 6:
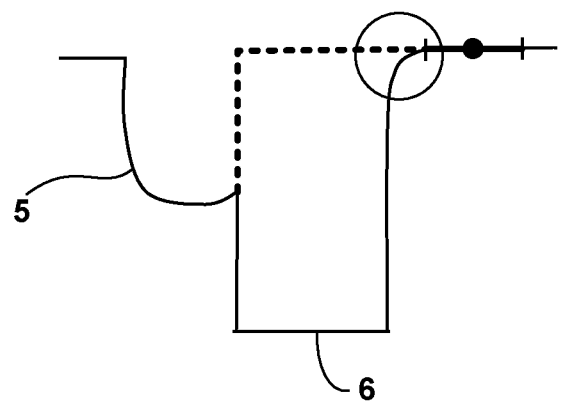
FIGS. 6 and 7 illustrate the possible configurations of processing of the image in the neighbourhood of the vents.
Figure 7:
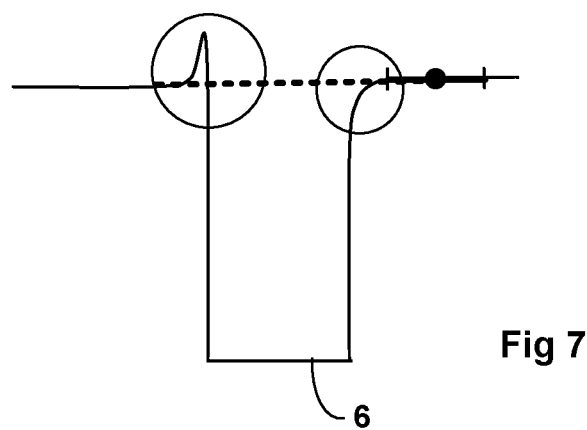
Figure 8:
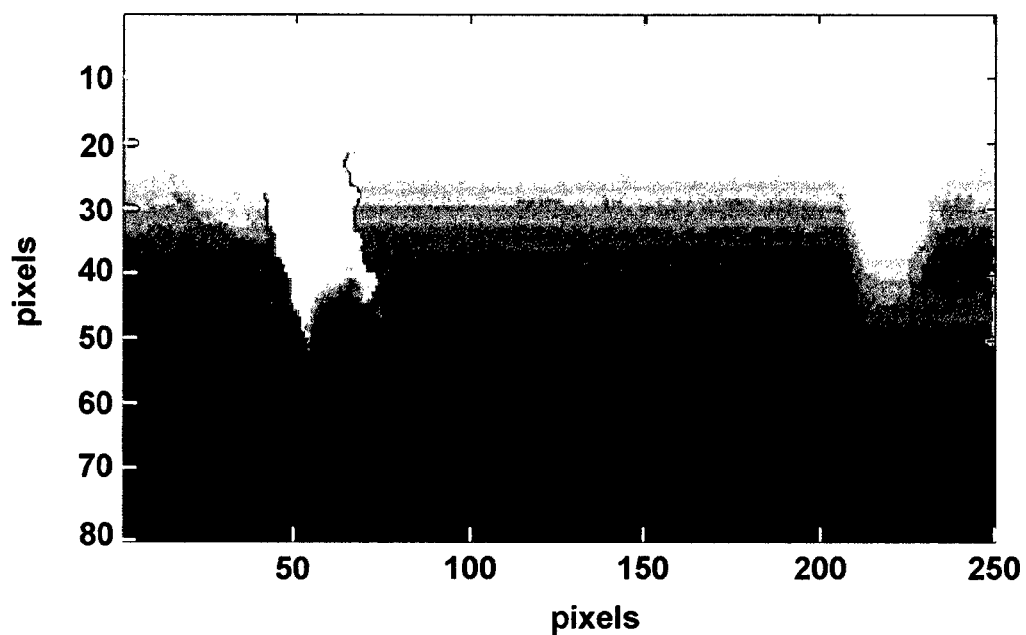
FIG. 8 represents the image of FIG. 4 after processing with the aid of the method according to the invention.

It is however observed that the contours of the zone containing the non-measurement points may experience alterations that it is judicious to correct during the implementation of this step. These alterations are materialized in the form of abnormal values placed above or below the mean grey level value, i.e. altitude of the points of the surface as is illustrated in FIG. 7 by circles surrounding the said zones. However, this phenomenon is not manifested when the boundary of the zone 6 containing the non-measurement points is adjoining the foot of the vent 5, as is illustrated in FIG. 6.

Hence, depending on the position of the row, slightly different correction strategies will be applied.

When the angle between the principal axis 60 of the said surface and the direction of the rows of pixels is less than 5°, that is to say when the zone is hardly inclined with respect to the rows and all the rows intersecting the shadow zone 6 also cut the foot of the vent, the mean grey level value of the pixels of the reference segment $s_i$ is assigned to the set of pixels of the row $l_i$ containing the said reference segment and lying between the middle m of the reference segment $s_i$ and the intersection of the said row of pixels with the contour of the vent.

To define the contour of the foot of the vent, it is considered that the pixel rows intersect the zone of non-measurement points. Each row $l_i$ intersects the said zone 6 at two points. A first point of intersection is situated on the edge of the said zone 6 on the side where the reference segment $s_i$ is situated. On the other hand, the second point of intersection is situated on the opposite edge of this zone of non-measurement points, and corresponds substantially to the point of intersection of the row comprising the said reference segment with the foot of the vent whose presence is at the origin of the shadow zone corresponding to the non-measurement points.

When the angle between the principal axis 60 of the said surface and the direction of the rows of pixels is greater than 5°, the zone containing the non-measurement points is then cut into two parts.

The first part contains the rows situated between the centre of gravity W and the foot of the vent 5. The mean grey level value of the pixels of the reference segment $s_i$ is then assigned to the set of pixels of the row $l_i$ containing the said reference segment $s_i$ and lying between the middle m of the reference segment and the intersection of the said row of pixels with the contour of the foot of the vent.

For the rows which do not lie between the centre of gravity W and the foot of the vent, the mean grey level value of the pixels of the reference segment $s_i$ is assigned to the set of pixels of the row $l_i$ containing the said reference segment $s_i$ and lying between the middle m of the reference segment and the pixel of the said row whose grey level value is lower than the mean grey level value of the pixels of the reference segment.

From experience, these different processings of the rows placed above and below the centre of gravity are specific to the particular problem of the vents situated on the surface of a tyre and make it possible to solve with little computation time the problematic issue of the non-measurement points.

FIG. 6 represents the image of the surface of the tyre after processing by the method according to the invention. It is observed that all the non-measurement points have disappeared, rendering the image able to be processed so as to extract therefrom information that may decide the orientation of the tyre.

The invention claimed is:

1. A method for processing an image of a surface of a tyre to be inspected, in which a three-dimensional digital image of the surface is acquired, in which each pixel of the acquired image is assigned a grey-level value proportional to an elevation of a corresponding point with respect to the surface, and in which pixels of the acquired image are placed in rows and columns, the method comprising:
digitally processing the image by using a computer processor to:
search the acquired image for zones of the surface, each of the zones including non-measurement points corresponding to pixels whose grey-level value is lower than a given threshold, the non-measurement points of each of the zones being erroneous points resulting from a shadow present when the image was being acquired;
determine boundaries of an encompassing box that includes one or more of the zones;
and,
correct the non-measurement points of the one or more of the zones inside the encompassing box by, for a given row (li) secant to a zone of the one or more of the zones, correcting the non-measurement points of the zone by assigning to each pixel of the zone a grey-level value equal to a mean grey-level value of a set (Kij, si) of pixels of a reference segment ($s_i$) belonging to the given row ($l_i$) and positioned in proximity to the zone,
wherein a result of the processing of the image is used to determine whether the tyre is in compliance with a reference.

2. The method according to claim 1, wherein the reference segment ($s_i$) does not include any pixel having a grey-level value lower than the given threshold.

3. The method according to claim 1, wherein a length of the reference segment ($s_i$) is between 5 and 30 pixels.

4. The method according to claim 1, wherein the mean grey-level value of the pixels of the reference segment ($s_i$) is assigned to the set of pixels of the given row ($l_i$) containing the reference segment ($s_i$) and having a grey-level value lower than the given threshold.

5. The method according to claim 1, wherein the processing of the image includes using the computer processor to:
   determine an area of the zone;
   when the area of the zone exceeds a given threshold, determine an angle between a principal axis of the zone and a direction of the rows of pixels;
   determine a centre of gravity of the zone;
   search for a position of a vent at an end of the principal axis of the zone, the zone being oriented in a direction (OX) extending along the zone and having a foot of the vent as an origin; and
   assign, to each row secant to the zone, a reference segment positioned on a side of the principal axis of the zone corresponding to an angular sector making a positive angle with the direction (OX).

6. The method according to claim 5, wherein, when the angle between the principal axis of the zone and the direction of the rows of pixels is less than 5°, the mean grey-level value of the pixels of the reference segment ($s_i$) is assigned to the set of pixels of the given row ($l_i$) containing the reference segment ($s_i$) and lying between a middle (m) of the reference segment ($s_i$) and an intersection of the given row ($l_i$) with a contour of the foot of the vent.

7. The method according to claim 5, wherein, when the angle between the principal axis of the zone and the direction of the rows of pixels is greater than 5°, and only for rows lying between centre of gravity and the foot of the vent, the mean grey-level value of the pixels of the reference segment ($s_i$) is assigned to the set of pixels of the given row ($l_i$) containing the reference segment ($s_i$), and lying between a middle (m) of the reference segment ($s_i$) and an intersection of the given row ($l_i$) with a contour of the foot of the vent.

8. The method according to claim 5, wherein, when the angle between the principal axis of the zone and the direction of the rows of pixels is greater than 5°, and for the rows that do not lie between the centre of gravity and the foot of the vent, the mean grey-level value of the pixels of the reference segment ($s_i$) is assigned to the set of pixels of the given row ($l_i$) containing the reference segment ($s_i$) and lying between a middle (m) of the reference segment ($s_i$) and a pixel of the given row ($l_i$) whose grey-level value is lower than the mean grey-level value of the pixels of the reference segment ($s_i$).

* * * * *